United States Patent [19]
Doong et al.

[11] Patent Number: 5,940,678
[45] Date of Patent: Aug. 17, 1999

[54] METHOD OF FORMING PRECISELY CROSS-SECTIONED ELECTRON-TRANSPARENT SAMPLES

[75] Inventors: Yih-Yuh Doong, Kaohsiung; Yong-Fen Hsieh, Hsinchu, both of Taiwan

[73] Assignee: United Microelectronics Corp., Taiwan

[21] Appl. No.: 08/927,322

[22] Filed: Sep. 11, 1997

[30]     Foreign Application Priority Data

Jan. 14, 1997  [TW]  Taiwan ................................. 86100334

[51] Int. Cl.⁶ ........................... G01R 31/26; H01L 21/66
[52] U.S. Cl. ................... 438/14; 438/22; 438/48
[58] Field of Search ................... 438/22, 14, 48

[56]         References Cited

U.S. PATENT DOCUMENTS

| | | |
|---|---|---|
| 4,098,917 | 7/1978 | Bullock et al. . |
| 4,503,329 | 3/1985 | Yamaguchi et al. . |
| 4,554,458 | 11/1985 | Behringer et al. . |
| 4,746,591 | 5/1988 | Kelly . |
| 5,316,979 | 5/1994 | MacDonald et al. ..................... 438/52 |
| 5,425,833 | 6/1995 | Fujimoto et al. . |
| 5,439,552 | 8/1995 | Moret ....................................... 438/52 |
| 5,520,769 | 5/1996 | Barrett et al. ............................ 438/14 |

*Primary Examiner*—Kevin M. Picardat
*Assistant Examiner*—Deven Cours
*Attorney, Agent, or Firm*—Rabin & Champagne, P.C.

[57]            ABSTRACT

A method of forming precisely cross-sectioned electron-transparent samples, includes removing, from a wafer, a chip containing a desired viewing site for analysis. At least one metallic mask is formed on a surface of the chip and over the viewing site using a focused ion beam microscope. Using a reactive ion etching technique, the chip is etched in a direction essentially perpendicular to the surface of the chip to form a thin viewing surface under the metallic mask. The thickness of the thin viewing surface is further reduced using a focused ion beam milling technique, to form an extremely thin electron-transparent sample.

32 Claims, 6 Drawing Sheets

METHOD OF FORMING PRECISELY CROSS-SECTIONED ELECTRON-TRANSPARENT SAMPLES

BACKGROUND OF THE INVENTION

1. Field of Invention

This invention relates in general to the checking and testing of semiconductor products using a charged particle microscope, and more particularly, to a method of forming precisely cross-sectioned electron-transparent samples which can be checked and tested using a charged particle microscope.

2. Description of Related Art

Cross-sectional side views of wafer chips are useful when investigating ultra large-scale integrated circuit components. Generally, sectioned samples are observed using electron or ion beam microscopes (also known as charged particle microscopes). For example, the most commonly used microscopes used for this task are scanning electron microscopes (SEM), transmission electron microscopes (TEM), scanning Auger microprobes (SAM) and focused ion beam (FIB) microscopes. When using these microscopes, the surface of the sample is bombarded with electrons or charged particles to create an observational image. Theoretically, the thinner the surface thickness of the sample, the better will be the resolution of the image viewed through the microscope.

A conventional method of preparing samples for observation using a charged particle microscope includes cleaving the wafer to form a wafer chip containing the feature to be investigated. Both faces of the wafer chip are polished using a chemical/mechanical polishing procedure until the targeted region is reached. This is followed by a lapping and a subsequent ion milling treatment to form a sample having a thickness of about 1000 Å or less.

One disadvantage of the aforementioned method is that only one specific location in each sample is targeted. Therefore, this known method is not suitable when a large number of viewing sites coexist in the same wafer chip. Furthermore, the quality of the sample is difficult to control during the chemical/mechanical polishing procedure, so that the yield rate is low.

Another conventional method of preparing samples for observation using a charged particle microscope is shown in FIGS. 1A through 1E. Referring to FIG. 1A, a cleft and chemical/mechanical polished wafer chip 14 is mounted onto a copper grid 12. Next, and referring to FIG. 1B, a layer of metal 16 is deposited over the desired viewing site using an FIB microscope. Thereafter, and as shown in FIG. 1C, an H-shaped metallic mask 18 is defined using a high current FIB milling operation. Next, a low current FIB milling operation is used to mill the wafer surface, until a thin viewing surface 19 having a thickness of about 1000 Å or less is obtained. The sample is now ready for observation under an electron microscope.

Referring to FIGS. 1D and 1E, when a wafer chip 14 has a plurality of desired viewing sites beneath its surface, an FIB microscope can be repeatedly used to deposit a plurality of metallic layers above the respective desired viewing sites. Then, the metallic layers can be similarly defined using FIB milling operations to form a plurality of H-shaped metallic masks 18'. Thereafter, FIB milling operations are again performed to further mill the wafer chip 14 in a plurality of locations, thereby forming a plurality of thin viewing surfaces 20 for observation with the electron microscope.

A major disadvantage of this method is that each milling operation can only form a viewing surface having a single desired thickness. Moreover, although the viewing surfaces are precisely obtained, each FIB milling operation is time consuming. For example, during the forming of viewing surfaces 20, the FIB milling operation must mill the wafer chip to a desired depth, and the viewing surfaces to the desired thickness. Thus, it may be too time consuming to completely prepare the sample when there are a plurality of viewing sites in the wafer chip.

SUMMARY OF THE INVENTION

It is an object of the present invention to provide a method of preparing precisely cross-sectioned electron-transparent samples using chemical/mechanical polishing, reactive ion etching and focused ion beam milling, in which the aforementioned disadvantages are avoided, that is, low yield due to the chemical/mechanical polishing operation, and extended periods of time spent in the preparation of samples using the FIB milling procedure.

The above and other objects are achieved by providing a method of forming precisely cross-sectioned electron-transparent samples, including removing, from a wafer, a chip containing a desired viewing site for analysis. At least one metallic mask is formed on a surface of the chip and over the viewing site using a focused ion beam microscope. Using a reactive ion etching technique, the chip is etched in a direction essentially perpendicular to the surface of the chip to form a thin viewing surface under the metallic mask. The thickness of the thin viewing surface is further reduced using a focused ion beam milling technique, to form an extremely thin electron-transparent sample.

The present invention allows for the simultaneous formation of a plurality of extremely thin viewing surfaces of desired viewing locations in the wafer chip for observation using a charged particle microscope. Additionally, the present invention can be used in both a non-production line and a production line environment.

BRIEF DESCRIPTION OF THE DRAWINGS

Other objects, features, and advantages of the present invention will become apparent from the following detailed description of the preferred but non-limiting embodiments. The description is made with reference to the accompanying drawings.

DESCRIPTION OF THE PREFERRED EMBODIMENTS

Figure 1A:
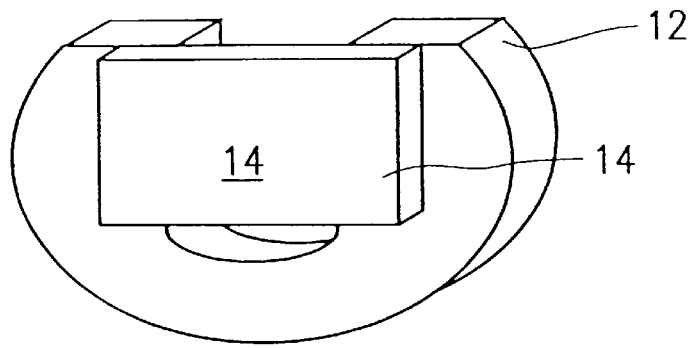
FIGS. 1A through 1E are a series of diagrams showing a conventional method of preparing an electron-transparent sample by milling a semiconductor component using a focused ion beam.
Figure 1B:
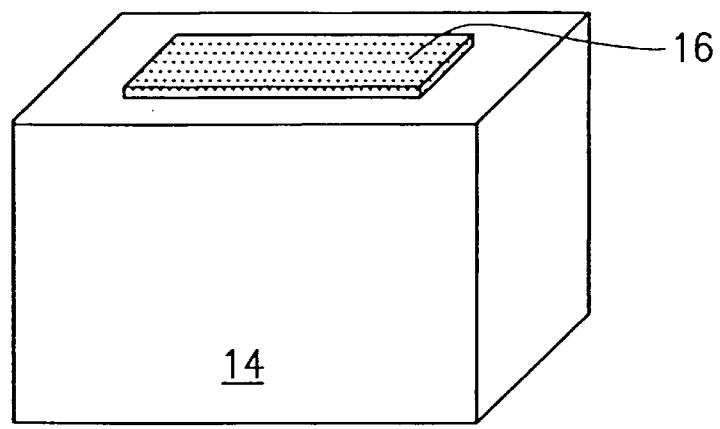
Figure 1C:
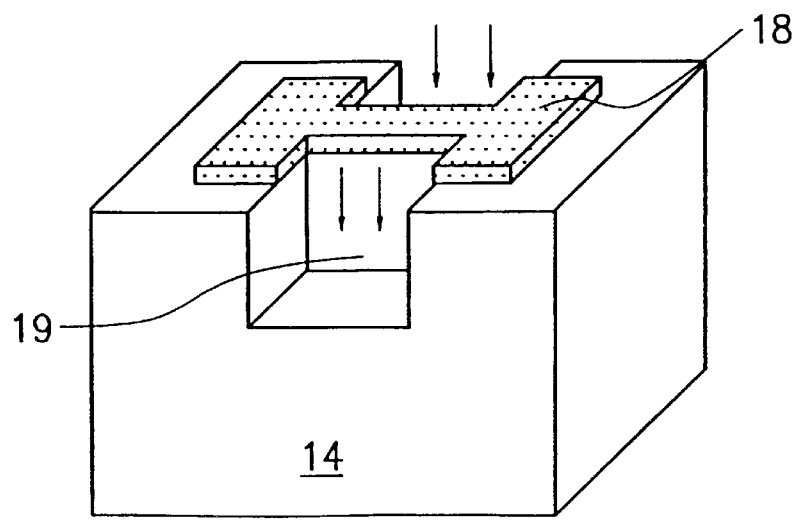
Figure 1D:
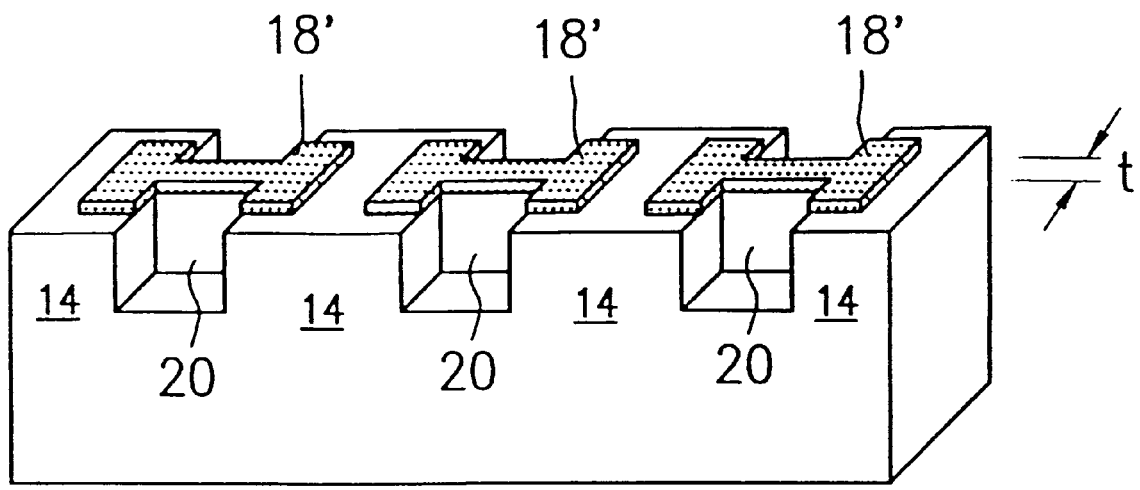
Figure 1E:
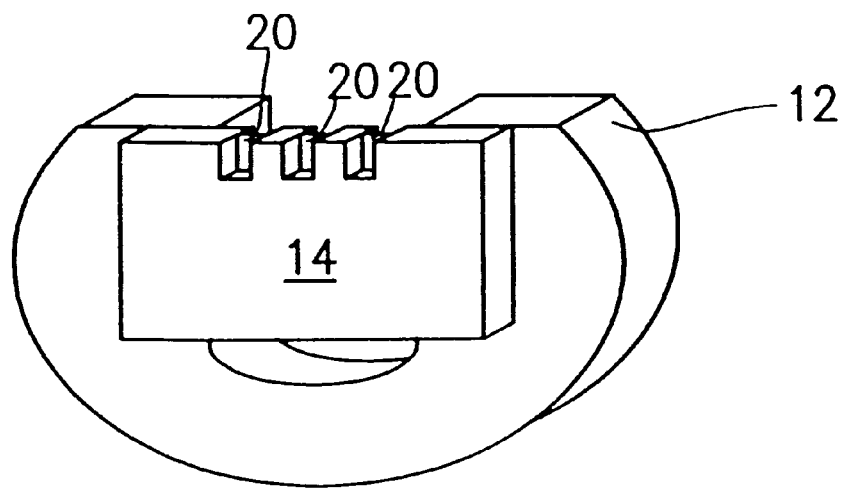
Figure 2A:
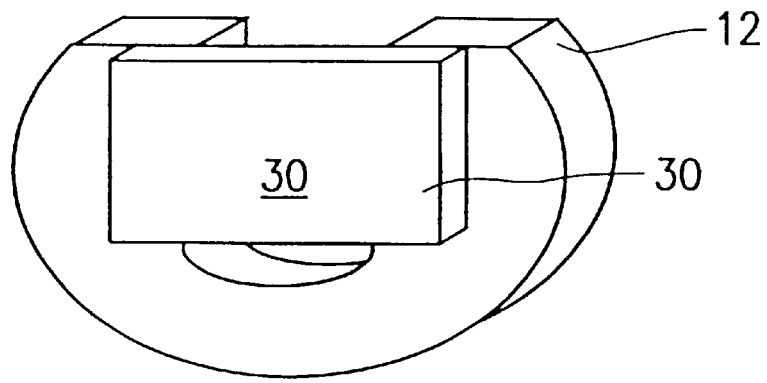
FIGS. 2A through 2F are a series of diagrams showing a method of preparing an electron-transparent sample or samples to be used in a non-production line, according to the present invention.

Referring to FIGS. 2A–2F, a first preferred embodiment of the present invention is shown, in which the electron-transparent sample is prepared for a non-production line. As shown in FIG. 2A, a cleft and chemical/mechanical polished wafer chip 30 having a thickness between about 20 $\mu$m and about 50 $\mu$m is mounted onto a copper grid 12, similar to that described in conjunction with FIG. 1A.

Figure 2B:
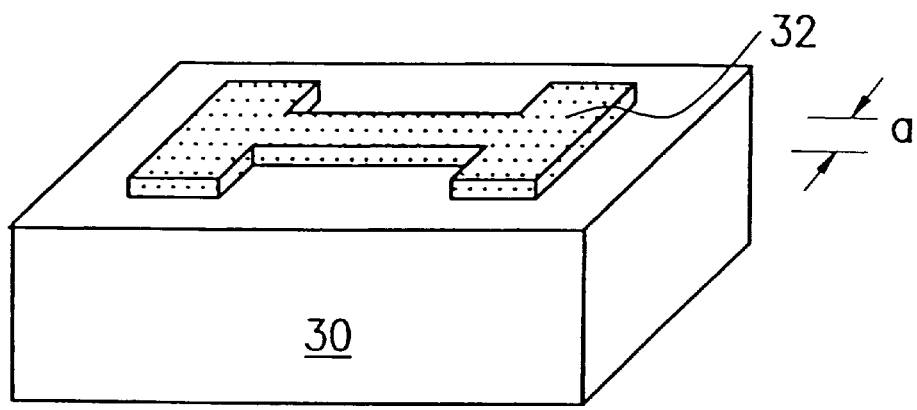

Next, and referring to FIG. 2B, an H-shaped metallic mask layer 32, having a narrowest width a of approximately 2 to 5 µm, is formed on the surface of the wafer chip 30 and over a desired viewing site, using an FIB microscope.

Figure 2C:
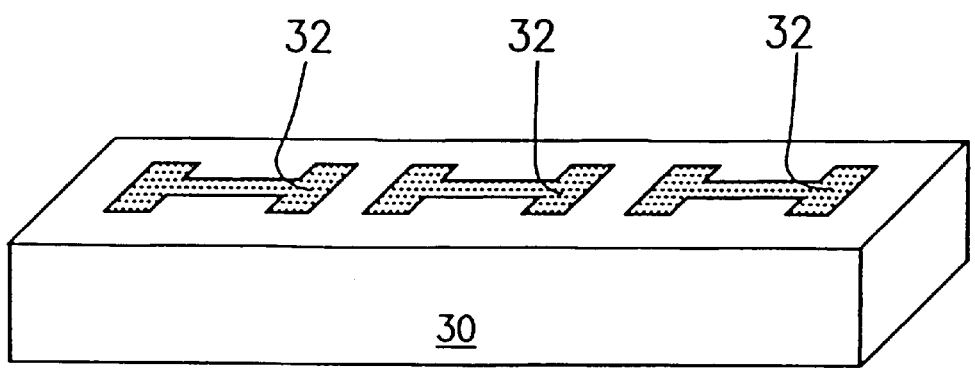

Referring to FIG. 2C, if there are a plurality of desired viewing sites on the wafer chip, the previous step is repeated to form a plurality of H-shaped metallic mask layers 32.

Figure 2D:
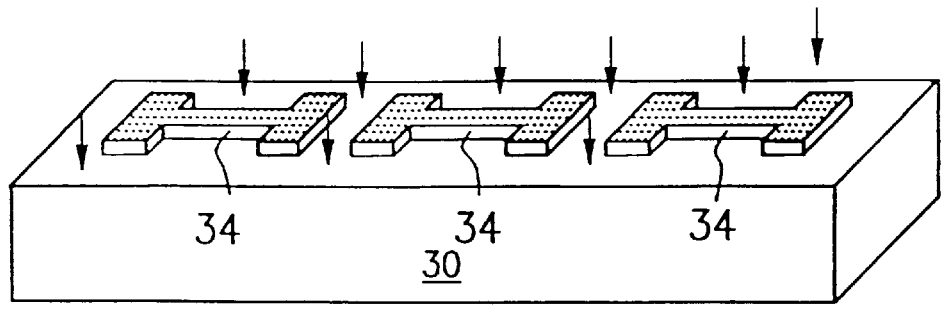

Referring next to FIG. 2D, reactive ion etching is performed to vertically etch areas of wafer chip 30 not covered by a metallic mask layer 32. As a result, a viewing surface 34 is formed underneath the respective metallic mask layer 32.

Figure 2E:
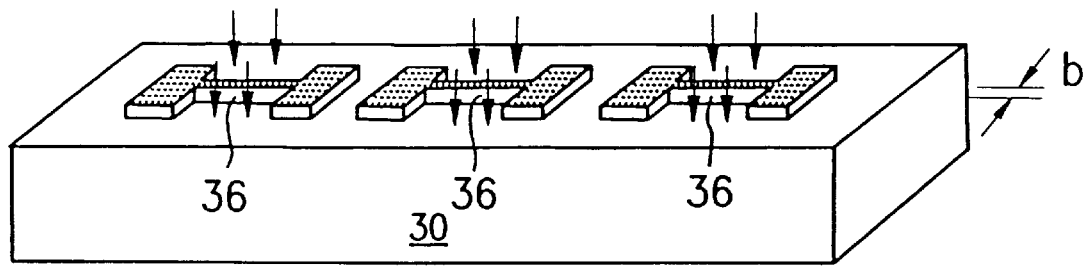

Referring to FIG. 2E, a focused ion beam is used to mill viewing surfaces 34, which further reduces the thickness of the viewing surfaces 34 to form precisely cross-sectioned electron-transparent samples 36, which have a thickness b of approximately 1000 Å or less, for example. Since only the viewing surfaces 34 are being milled, this procedure is performed relatively quickly.

Figure 2F:
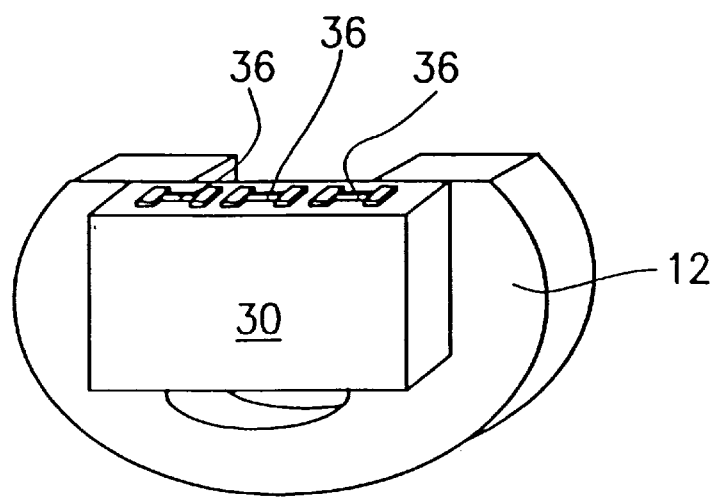

Referring to FIG. 2F, the precisely cross-sectioned electron-transparent samples 36, mounted onto copper grid 12, are subsequently observed using an electron microscope.

In this embodiment, the chemical/mechanical polishing operation can be performed immediately after cleaving the wafer chip 30, or postponed until after the ion etching operation is performed. In this example, the chemical/mechanical polishing operation was performed immediately after cleaving the wafer chip 30.

Referring to FIGS. 3A–3F, a second preferred embodiment of the present invention is shown, in which the electron-transparent sample is prepared for a production line.

Figure 3A:
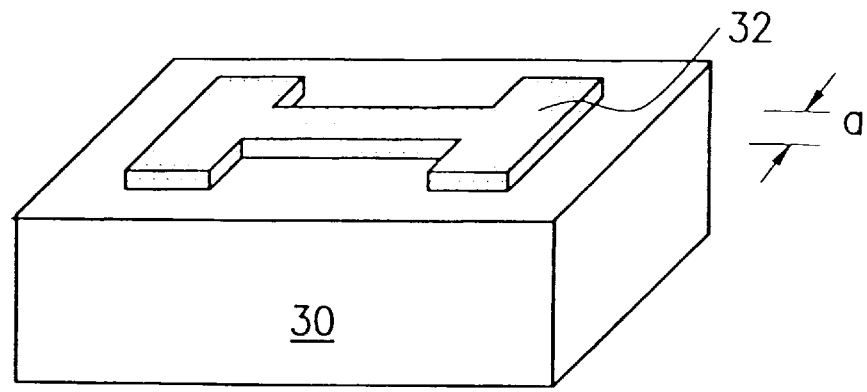
FIGS. 3A through 3F are a series of diagrams showing a method of preparing an electron-transparent sample or samples to be used in a production line, according to the present invention.

As shown in FIG. 3A, a metallic layer is deposited on the surface of the wafer chip 30 using a focused ion beam microscope. Next, using photolithographic and etching techniques, a pattern is defined to form an H-shaped metallic mask 32, having a narrowest width a of approximately 2 to 5 µm.

Figure 3B:
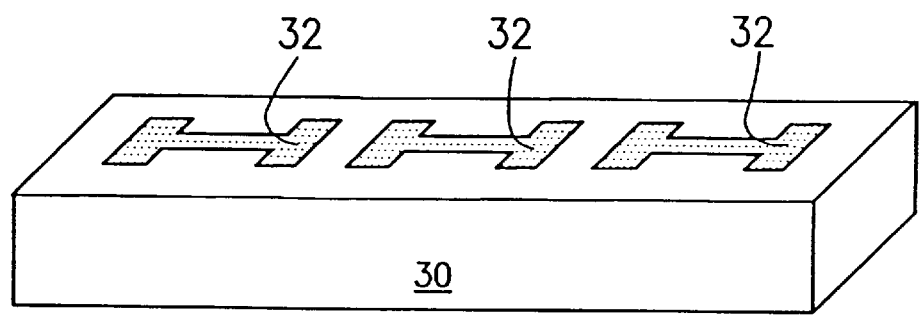

As shown in FIG. 3B, if there are a plurality of desired viewing sites on the wafer chip 30, the previous step is repeated to form a plurality of H-shaped metallic mask layers 32.

Figure 3C:
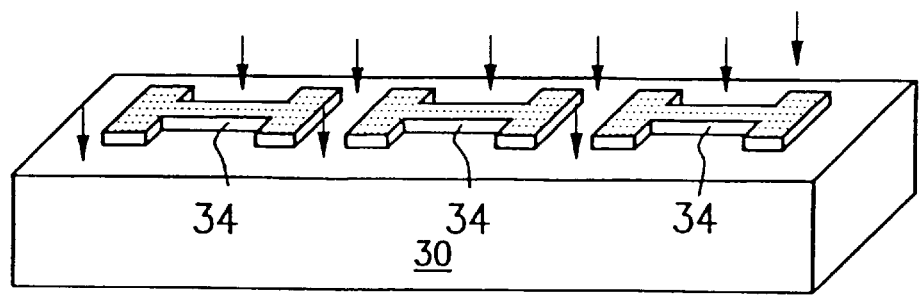

Referring next to FIG. 3C, reactive ion etching is performed to vertically etch areas of wafer chip 30 not covered by a metallic mask layer 32. As a result, a viewing surface 34 is formed underneath the respective metallic mask layer 32.

Figure 3D:
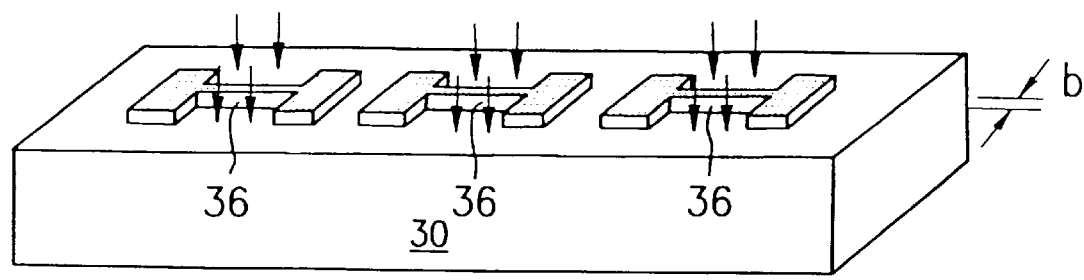

Referring to FIG. 3D, a focused ion beam is used to mill viewing surfaces 34, which further reduces the thickness of the viewing surfaces 34 to form precisely cross-sectioned electron-transparent samples 36, which have a thickness b of approximately 1000 Å or less, for example.

Figure 3E:
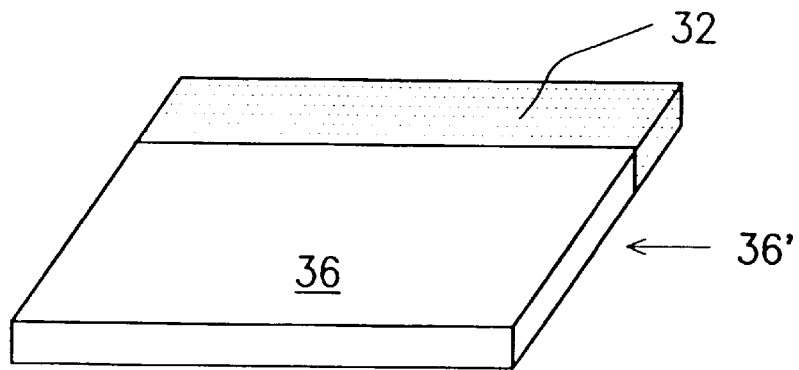

As shown in FIG. 3E, in a subsequent step, individual thin viewing sections 36' are cleft out, i.e. removed, each of such viewing section including a precisely cross-sectioned electron-transparent sample 36 with a layer of metallic mask 32 attached to its top.

Figure 3F:
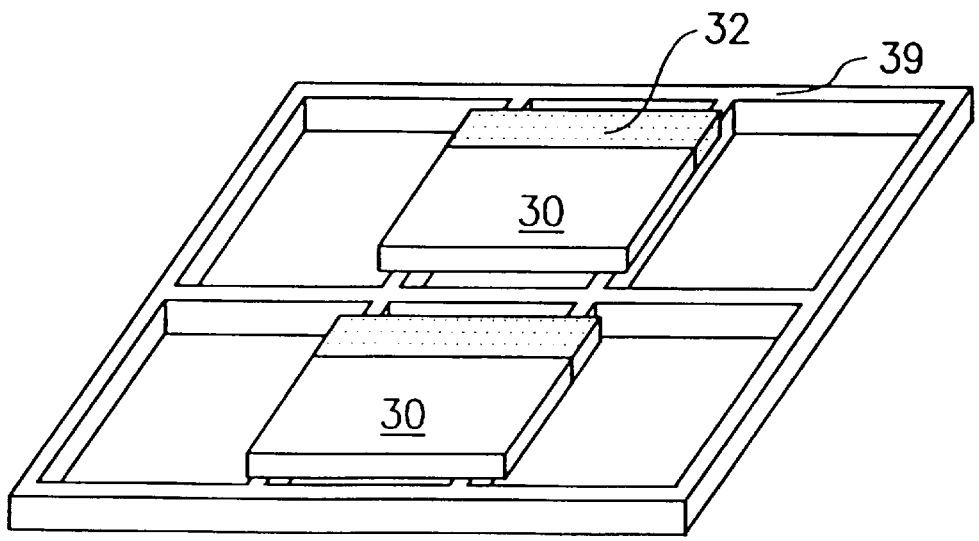

Referring to FIG. 3F, each individual thin viewing section 36' is placed on a net frame 39, for observation using an electron microscope.

Similar to the first embodiment, a chemical/mechanical polishing operation can be performed immediately after cleaving the wafer chip 30, or postponed until after the ion etching operation is performed.

While the present invention has been described by way of example and in terms of the preferred embodiments, it is to be understood that the invention is not limited to the disclosed embodiments. To the contrary, it is intended to cover various modifications and similar arrangements as would be apparent to one of ordinary skill in the art. Therefore, the scope of the appended claims, which define the invention, should be accorded the broadest interpretation so as to encompass all such modifications and similar structures.

What is claimed is:

1. A method of forming precisely cross-sectioned electron-transparent samples, comprising:

removing, from a wafer, a chip containing a desired viewing site;

forming at least one metallic mask on a surface of the chip and over the viewing site;

reactive ion etching the chip in a direction essentially perpendicular to the surface of the chip to form a thin viewing surface under the metallic mask; and further reducing the thickness of the thin viewing surface, using a focused ion beam milling technique, to form an extremely thin electron-transparent sample.

2. The method recited in claim 1, wherein said removing includes cleaving the chip from the wafer.

3. The method recited in claim 1, wherein said forming at least one metallic mask includes forming a plurality of metallic masks over a plurality of respective viewing sites located within a single chip.

4. The method recited in claim 1, further comprising polishing and lapping the surface of the chip after said removing and before said forming.

5. The method recited in claim 4, wherein, after said polishing and lapping, the chip has a thickness of approximately 20 to 50 µm.

6. The method recited in claim 5, wherein the metallic mask has a narrowest width of approximately 2 to 5 µm.

7. The method recited in claim 6, wherein the electron-transparent sample has a thickness of approximately 1000 Å or less.

8. The method recited in claim 7, wherein said forming at least one metallic mask includes forming a plurality of metallic masks over a plurality of respective viewing sites located within a single chip so as to form a plurality of extremely thin electron-transparent samples.

9. The method recited in claim 4, further comprising removing the extremely thin electron-transparent sample from the chip after said further reducing.

10. The method recited in claim 9, wherein the chip has a thickness of approximately 20 to 50 µm after said polishing and lapping.

11. The method recited in claim 10, wherein the metallic mask has a narrowest width of approximately 2 to 5 µm.

12. The method recited in claim 11, wherein the electron-transparent sample has a thickness of approximately 1000 Å or less.

13. The method recited in claim 12, wherein said forming at least one metallic mask includes forming a plurality of metallic masks over a plurality of respective viewing sites located within a single chip, so as to form a plurality of extremely thin electron-transparent samples.

14. The method recited in claim 9, wherein said removing the extremely thin electron-transparent sample includes cleaving the sample from the chip.

15. The method recited in claim 1, further comprising polishing and lapping the surface of the chip after said etching and before said further reducing.

16. The method recited in claim 15, wherein the metallic mask has a narrowest width of approximately 2 to 5 µm.

17. The method recited in claim 16, wherein the chip has a thickness of approximately 20 to 50 μm after said polishing and lapping.

18. The method recited in claim 17, wherein the electron-transparent sample has a thickness of approximately 1000 Å or less.

19. The method recited in claim 18, wherein said forming at least one metallic mask includes forming a plurality of metallic masks over a plurality of respective viewing sites located within a single chip so as to form a plurality of extremely thin electron-transparent samples.

20. The method recited in claim 15, further comprising removing the extremely thin electron-transparent sample from the chip after said further reducing.

21. The method recited in claim 20, wherein the metallic mask has a narrowest width of approximately 2 to 5 μm.

22. The method recited in claim 21, wherein the chip has a thickness of approximately 20 to 50 μm after said polishing and lapping.

23. The method recited in claim 22, wherein the electron-transparent sample has a thickness of approximately 1000 Å or less.

24. The method recited in claim 23, wherein said forming at least one metallic mask includes forming a plurality of metallic masks over a plurality of respective viewing sites located within a single chip, so as to form a plurality of extremely thin electron-transparent samples.

25. The method recited in claim 20, wherein said removing the extremely thin-electron-transparent sample includes cleaving the sample from the chip.

26. The method recited in claim 1, wherein said forming includes using a focused ion beam microscope.

27. A method of forming precisely cross-sectioned electron-transparent samples, comprising:

forming at least one metallic mask on a surface of a wafer and over a viewing site using a focused ion beam microscope;

reactive ion etching the wafer in a direction essentially perpendicular to the surface of the wafer to form a thin viewing surface under the metallic mask;

further reducing the thickness of the thin viewing surface, using a focused ion beam milling technique, to form an extremely thin electron-transparent sample; and cleaving the extremely thin electron-transparent sample from the wafer after said further reducing.

28. The method recited in claim 27, wherein the metallic mask has a narrowest width of approximately 2 to 5 μm.

29. The method recited in claim 28, wherein the electron-transparent sample has a thickness of approximately 1000 Å or less.

30. The method recited in claim 29, wherein said forming at least one metallic mask includes forming a plurality of metallic masks over a plurality of respective viewing sites located within a single wafer, so as to form a plurality of extremely thin electron-transparent samples.

31. The method recited in claim 1, wherein the thin viewing surface is flat.

32. The method recited in claim 27, wherein the thin viewing surface is flat.

* * * * *